United States Patent [19]
Biskup et al.

[11] Patent Number: 5,849,947
[45] Date of Patent: Dec. 15, 1998

[54] PROCESS FOR THE PREPARATION OF TOLUYLENE DIISOCYANATE, SPECIFIC MIXTURES OF TOLUYLENE DIAMINE AND WATER, AND THE USE OF TOLUYLENE DIAMINE AND WATER MIXTURES TO PREPARE TOLUYLENE DIISOCYANATE

[75] Inventors: Klaus Biskup, Leverkusen; Berthold Keggenhoff, Krefeld, both of Germany

[73] Assignee: Bayer Aktiengesellschaft, Leverkusen, Germany

[21] Appl. No.: 691,222

[22] Filed: Aug. 1, 1996

[30] Foreign Application Priority Data

Aug. 4, 1995 [DE] Germany ......................... 195 28 781.9

[51] Int. Cl.$^6$ .................................................. C07C 211/50
[52] U.S. Cl. ............................................ 560/347; 564/422
[58] Field of Search ............................... 564/422; 560/347

[56] References Cited

U.S. PATENT DOCUMENTS

| | | |
|---|---|---|
| 2,976,320 | 3/1961 | Winstrom ................................. 564/422 |
| 4,224,249 | 9/1980 | Kunz ....................................... 564/422 |
| 4,717,774 | 1/1988 | Narayan et al. ......................... 564/422 |
| 5,449,832 | 9/1995 | Van Court Carr et al. ............. 564/422 |
| 5,693,862 | 12/1997 | Keyvani et al. ........................ 564/305 |
| 5,714,634 | 2/1998 | Casale et al. ............................ 564/422 |

FOREIGN PATENT DOCUMENTS

| | | |
|---|---|---|
| 2142911 | 3/1994 | Canada . |
| 895197 | 5/1962 | United Kingdom ................... 564/422 |
| 1164519 | 9/1969 | United Kingdom . |

*Primary Examiner*—Robert Gerstl
*Attorney, Agent, or Firm*—Joseph C. Gil; N. Denise Brown

[57] ABSTRACT

Toluylene diisocyanate is produced by nitration of toluene toy yield dinitrotoluene, hydrogenation of the dinitrotoluene, optionally in the presence of a solvent or diluent, to yield a crude solution of toluylene diamine and reaction water, processing the crude solution of toluylene diamine and water to yield an intermediate mixture of toluylene diamine and water wherein the processing is interrupted to result in a water content of about 1–40% by weight, preferably about 2–10% by weight of the intermediate mixture, transporting this intermediate mixture from a first production facility to a second production facility, whereat the intermediate mixture of TDA and water is completed to yield dry toluylene diamine of commercial quality, and followed by phosgenation of the toluylene diamine to give toluylene diisocyanate. It is optional to additionally process the dry toluylene diamine prior to phosgenation. The invention also relates to intermediate mixtures of toluylene diamine and water which have a solidification point of at most 95° C., and the use of these intermediate mixtures for producing toluylene diisocyanate. It is preferable that the use of these intermediate mixtures to produce toluylene diisocyanate is performed at a site (or location) which is different from the site of production of the intermediate mixtures of toluylene diamine and water.

7 Claims, 4 Drawing Sheets

PROCESS FOR THE PREPARATION OF TOLUYLENE DIISOCYANATE, SPECIFIC MIXTURES OF TOLUYLENE DIAMINE AND WATER, AND THE USE OF TOLUYLENE DIAMINE AND WATER MIXTURES TO PREPARE TOLUYLENE DIISOCYANATE

BACKGROUND OF THE INVENTION

The present invention relates to a process for the preparation of toluylene diisocyanate (TDI). This process comprises reacting toluene with nitric acid to yield dinitrotoluene (DNT), hydrogenating the resultant dinitrotoluene (DNT) to yield toluylene diamine (TDA) and reaction water, and reacting the toluylene diamine with phosgene to give TDI. However, the process steps to form toluylene diamine (TDA) are performed in a first production plant wherein the crude solution of toluylene diamine (TDA) and water from the hydrogenation step is distilled to form an intermediate mixture of toluylene diamine and water containing about 1 to 40% by weight of water. This intermediate mixture is transported to a second production plant located at some distance from the first plant. In the second production plant, the distillation of the intermediate mixture of toluylene diamine (TDA) and water is completed to yield dry toluylene diamine, which is then phosgenated to yield toluylene diisocyanate (TDI).

The present invention also relates to specific mixtures of toluylene diamine and water, and to the use of these mixtures to prepare toluylene diisocyanate at a location which is different from the location at which the mixture of toluylene diamine and water has been obtained or prepared.

Normally the large-scale production of TDI is performed using the process stages of reacting toluene with nitric acid to yield DNT and water, reacting the DNT with hydrogen to yield TDA and water, followed by reacting the processed, dried TDA with phosgene to yield TDI and hydrogen chloride wherein the production units for each stage of the process are linked to each other in one production plant.

It may be advantageous, however, to perform the process steps in two production plants located at some distance from each other, wherein the process stages up to the production of TDA are performed in one production plant and the reaction of TDA with phosgene and processing to give a marketable TDI final product are performed in the second production plant. This type of procedure may be economically attractive if, for instance, suitable raw materials and infrastructures are readily available in one area, but a large purchasing market with the necessity for local production of the final product is provided in another area located a considerable distance away. Furthermore, it may also be economically advantageous to supply a variety of small phosgene units in various locations from one central, integrated amine plant located some distance away.

This mode of production and/or operation is made considerably more difficult, however, by the fact that the intermediate product, TDA, has a high melting point. This means that TDA can be transported only either in the solid form or as a hot melt at a temperature of more than 100° C. When transporting TDA in the solid form, the TDA first has to be subjected to an expensive processing stage such as, for example, to produce flakes, in order to be able to melt the product again after transportation for use in its final phosgenation reaction. On the other hand, overseas transport as a hot melt requires the use of heatable tank containers and appropriate heating facilities on board ship such as, for example, connections for heating steam or for electrical power, or, in the case of transportation as bulk goods, the use of tanker ships whose holds can be heated to a temperature of 105°–110° C. The first case, which requires use of heatable tank containers, is very expensive and uneconomical for the transportation of large amounts of TDA. In the second case, transportation as bulk goods in ships with heatable holds, would also be very expensive and, therefore, uneconomical because conventional tanker ships and the trans-shipment devices in docks are not intended for use at high temperatures. This method would first require the tanker ships and trans-shipment devices to be adapted for this purpose, which would be a great expense. Finally the problem of disposing of the slops from the ships' holds, optionally, by means of expensive special waste incineration procedures on land, would have to be overcome.

U.S. Pat. No. 5,449,832 describes one process for storing and transporting toluenediamine (TDA). This process comprises dinitrating toluene to yield the 2,4- and 2,6-isomers of dinitrotoluene, hydrogenating the dinitrotoluene to yield the 2,4- and 2,6-isomers of toluenediamine, and distilling the toluenediamine to produce essentially anhydrous product of 2,4- and 2,6-toluenediamine, which is then cooled and transferred for storage and/or shipment. Prior to storing and/or shipping the toluenediamine (TDA), the melting point of the TDA is reduced by adding water in an amount of about 5 to 15%, preferably 7 to 10% by weight (based on the weight of anhydrous TDA), and controlling the temperature of the resultant TDA-water mixture such that the final temperature of the TDA-water mixture is at or below the boiling point. It is this mixture which is suitable for long term storage and/or transport. The water added to the anhydrous TDA is hot demineralized water, a deionized water, or distilled water under pressure. The final temperature level from the addition of water to the anhydrous TDA provides sufficient internal heat to maintain the TDA-water mixture in a liquid state for an extended time period, and thus, allow for storage and/or transportation of the mixture.

SUMMARY OF THE INVENTION

The present invention provides TDA formulations which can be stored or transported in liquid form at a temperature below 95° C. without solids settling out.

A further object is to modify the process for the production of TDI by nitration of toluene to yield DNT, hydrogenation of DNT to yield TDA and water, and reaction of dried TDA with phosgene to yield TDI in such a manner that it is possible to transport the TDA in tanker containers or as bulk goods from a first production plant to a second production plant located some distance away, without the disadvantages mentioned above.

This object is achieved by the mixtures and process of the present invention.

It has now, surprisingly, been shown that specific mixtures of TDA and water, having a water content of 1–40%, preferably 2–10%, have clearly depressed melting points and are thus substantially easier to handle and are more cost-effective to transport over long distances as bulk goods in tanker ships than is pure TDA. Tanker ships designed for transporting chemicals are generally able to maintain the goods which are being transported at temperatures in the range of about 65° to 70° C. during transportation, and also to unload the chemicals over a similar temperature range. Thus, one object of the process according to the invention is to obtain TDA/water mixtures whose melt characteristics enable their transportation as bulk goods in conventional tanker ships.

Mixtures in accordance with the invention may be produced, in principle, by mixing pure TDA, i.e. conventional industrial isomer mixtures containing about 80 wt. % of 2,4 TDA and about 20 wt. % of 2,TDA, with water. These mixtures are more readily accessible, however, if during the distillation step of the hydrogenation product which contains TDA and water, the industrial process is interrupted at a suitable point such that an intermediate mixture of TDA and water, having a water content of about 1 to 40% by weight, is obtained instead of anhydrous TDA as in conventional processes.

Thus, the present invention provides a process for the production of toluylene diisocyanate comprising reacting toluene with nitric acid to yield dinitrotoluene, hydrogenating the dinitrotoluene to yield a crude solution of toluylene diamine and reaction water, and distilling the crude solution of toluylene diamine and reaction water to form an intermediate mixture of toluylene diamine and water which contains from about 1 to 40%, preferably about 2 to 10% by weight of water, then transporting this intermediate mixture of toluylene diamine and water from a first production plant to a second production plant, followed by distilling the intermediate mixture of toluylene diamine and water completely at the second production plant to yield dry toluylene diamine, and phosgenating the dry toluylene diamine to yield toluylene diisocyanate.

In another embodiment, the dinitrotoluene is hydrogenated in the presence of a solvent or diluent. This solvent or diluent may be either completely or partially removed or separated from the crude solution of toluylene diamine and reaction water in an additional step prior to distilling the crude solution of toluylene diamine and reaction water to yield the intermediate mixture of toluylene diamine and water which is suitable for storage and/or transportation.

In another embodiment, the dried toluylene diamine, after being completely distilled at a second production plant, may be subjected to further processing stages prior to phosgenation to yield toluylene diisocyanate in a manner known per se.

DETAILED DESCRIPTION OF THE INVENTION

Figure 1:
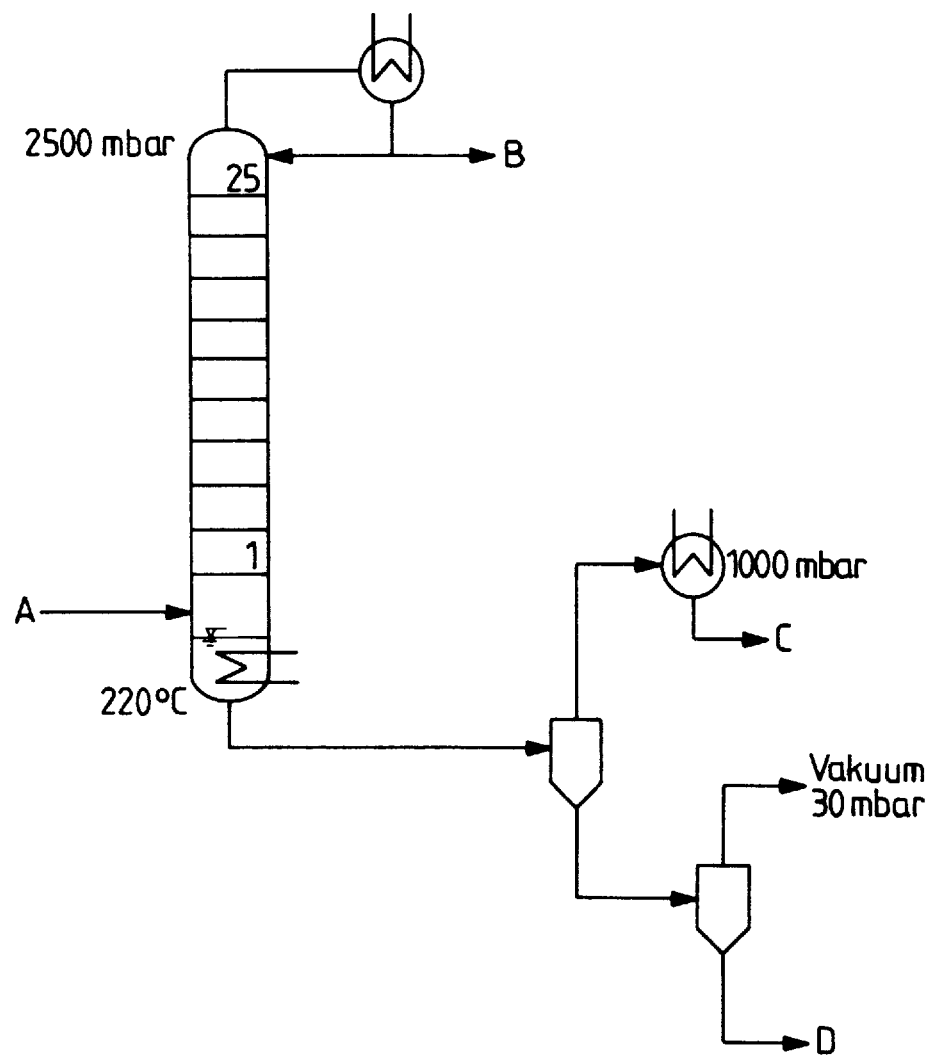
FIG. 1 is a schematic diagram illustrating water removal from crude solutions of TDA and water to yield dry TDA in the traditional process as described in the prior art.

According to the present invention, it is preferred that:
the toluylene diamine comprises 2,4-toluylene diamine, 2,6-toluylene diamine or any mixture of these isomers, and, optionally, with 2,3-toluylene diamine, 3,4-toluylene diamine, or mixtures thereof, in any quantity, and
no solvent or diluent is present during the hydrogenation of the dinitrotoluene.

The invention also relates to mixtures of toluylene diamine and water wherein the solidification point of these mixtures is at most 95° C.

According to the invention, the mixtures with a solidification point in the range of about 60°–95° C., more preferably 65°–70° C.,
which consist of 2,4- and/or 2,6-toluylene diamine and water, and
which contain 1 to 40% by weight, more preferably 2 to 10% by weight, based on 100% by weight of the mixture of toluylene diamine and reaction water are preferred.

In addition to the water content given above, the mixtures according to the invention may, optionally, contain a maximum concentration of organic, homogeneously dissolved solvent or diluent of about 10 wt. %. Suitable solvents or diluents in this case are, in particular, lower alcohols, preferably methanol, ethanol, n-propanol and isopropanol, lower ketones, specifically acetone, and diols, specifically ethylene glycol, or also toluene.

The invention also provides use of the intermediate mixtures of TDA and water to prepare toluylene diisocyanate by phosgenation, with prior removal of the water.

It is preferred that the intermediate mixtures intended for preparing toluylene diisocyanate are transported to a production plant which is spatially displaced from the site of preparation of the mixtures.

Industrial production of TDA from dinitrotoluene is generally achieved using a continuous process by reducing the nitrogen groups in DNT with hydrogen under high pressure on a suspended, powdered catalyst such as, for example, palladium on activated carbon or Raney nickel, and optionally in the presence of a diluent or solvent. A large number of processes for preparing aromatic amines such as TDA by catalytic hydrogenation of the corresponding nitro compound, DNT, in the present invention, have been disclosed. These processes are described in, for example, DE-OS 1,542,544, 1,947,851, 2,016,644, 2,135,154, 2,214,056, 2,456,308, BE PS 631,964, 661,047, 661,946, FR-PS 1,359,438, GB-PS 768,111, EP-A 0,124,010.

Suitable solvents or diluents include compounds such as, for example, methanol, ethanol or propanol (Ullmann, 4th ed., 1977, vol. 13, p. 14). The presence of these solvents or diluents helps to distribute the high heat of reaction (of about 418 kJ per mole of nitro groups) throughout a large amount of reaction material and to facilitate its removal as well as to increase the availability of dinitrotoluene in suspension by improving the solubility. Running counter to these desirable properties, is the presence of solvents is associated with additional distillation costs for their separation. Thus, minimizing the use of solvent while simultaneously observing the safety and reaction requirements of this stage represents an optimizing target. Accordingly, the continuous production of TDA without the use of solvents is preferred for the process according to the invention, as is possible using the reactors in accordance with U.S. Pat. No. 5,387,396, the disclosure of which is herein incorporated by reference, (believed to correspond to DE-OS 3,635,217). These reactors are constructed in such a way that they enable particularly efficient removal of heat by means of evaporation cooling, i.e. by the production of, for instance, water vapor on the coolant side. Thus in the case of dinitrotoluene, these reactors permit the reaction to be performed at a higher temperature than is otherwise normal, that is at 180°–200° C. instead of 100°–150° C., and without the use of a solvent.

The crude solution obtained during reaction of dinitrotoluene with hydrogen comprises about 60 wt. % TDA with about 40 wt. % reaction water and, optionally, used diluent or solvent. This crude solution also contains, after isolation of the solid catalyst such as, for example, by filtration or sedimentation, the by-products of the process. These by-products are mainly 2,3-TDA and 3,4-TDA, and may account for about 3 to 5 wt. % of crude solution. Other by-products may also exist, including some which have high molecular weights. In order to prepare a suitable starting product which can be used for phosgenation, water and, optionally, any diluent or solvent present must be completely removed in a manner known per se such as, for example, by distillation. In addition, in order to obtain the highest possible yield of TDI, it is also expedient to remove the by-products by distillation, whereupon the conventional purity of commercially available TDA is obtained. Conventional pure TDA comprises about 80% by weight of 2,4-toluylene diamine and about 20% by weight of 2,6-toluylene diamine.

Before removing the reaction water which is produced during the hydrogenation of dinitrotoluene, any solvent present must first be removed from the crude, catalyst-free, solution of toluylene diamine (TDA) and reaction water. Removal of the solvent generally takes place, in a known manner, by distillation in a continuously operated distillation column, wherein the solvent is recovered in such a state of purity, by means of process management, that it can be re-used directly in the process without further purification. It is also possible to separate, from the crude solution of TDA and reaction water, the solvent together with some (or all) of the water formed by means of distillation, and then to recover the solvent with the required degree of purity from the mixture of solvent and water in a further process stage. When performing the reaction without adding solvent, solvent isolation is obviously not required.

In a conventional industrial process for the production of toluylene diisocyanate (TDI), the drying procedure of the crude solution of TDA and water then follows. This procedure completely removes all of the reaction water which is present in the crude solution of TDA and reaction water. The water generally accounts for up to about 40 wt. % of the crude solution. In principle, this may be achieved by simply driving off the water by heating the crude solution under vacuum and withdrawing the vapors which are formed. However, the isolated water obtained by this simple procedure is not produced in the purity required for straightforward waste disposal, but is always more or less contaminated with TDA. Accordingly, it is better to remove the reaction water by distillation in an appropriate distillation apparatus. In this case, for example, the crude solution of TDA and reaction water is heated to a temperature of more than 200° C. at the base of a column, thus producing water in pure form at the head of the column. These distillation columns used in conventional processes are operated at atmospheric pressure or with a slight excess pressure, have about 20 to 30 bubble plates (i.e. practical plates), and the TDA is withdrawn from the base, with the last traces of water being removed by decompressing into a vacuum of 30 to 50 mbar.

FIG. 1 is a schematic diagram of the traditional process (i.e. prior art process) for the removal of water from TDA. In FIG. 1:

A represents: crude solution of TDA and water which contains about 60 wt. % TDA;

B represents: water withdrawal;

C represents: TDA/water mixture returned to A;

D represents: TDA (dry) withdrawal;

and 25 represents: the number of bubble plates in the distillation column.

The present invention, however, differs from the conventional course of the process for producing TDA described above. More specifically, the present invention differs from conventional processes in that the step of separating the water from the crude solution of TDA and reaction water is performed in two steps. In fact, the crude solution of TDA and reaction water, which contains about 40 wt. % of water, has the very depressed solidification point of about 45° C. Therefore, this crude solution of TDA and reaction water would be suitable for bulk transportation in tanker ships. The solidification point, as used herein, is understood to be the temperature at which the transition from a liquid state to a solid state takes place. However, transporting the crude solution of TDA and reaction water would mean that expensive cargo space would be largely wasted on the transportation of water.

In the process according to the invention, therefore, partial removal of reaction water from the crude solution of TDA and reaction water is performed to yield an intermediate mixture of TDA and water, wherein the residual concentration of water in the intermediate mixture is adjusted so that the solidification point of the resulting intermediate mixture is not above that of the controlled temperature range normally utilized in tanker ships.

Figure 3:
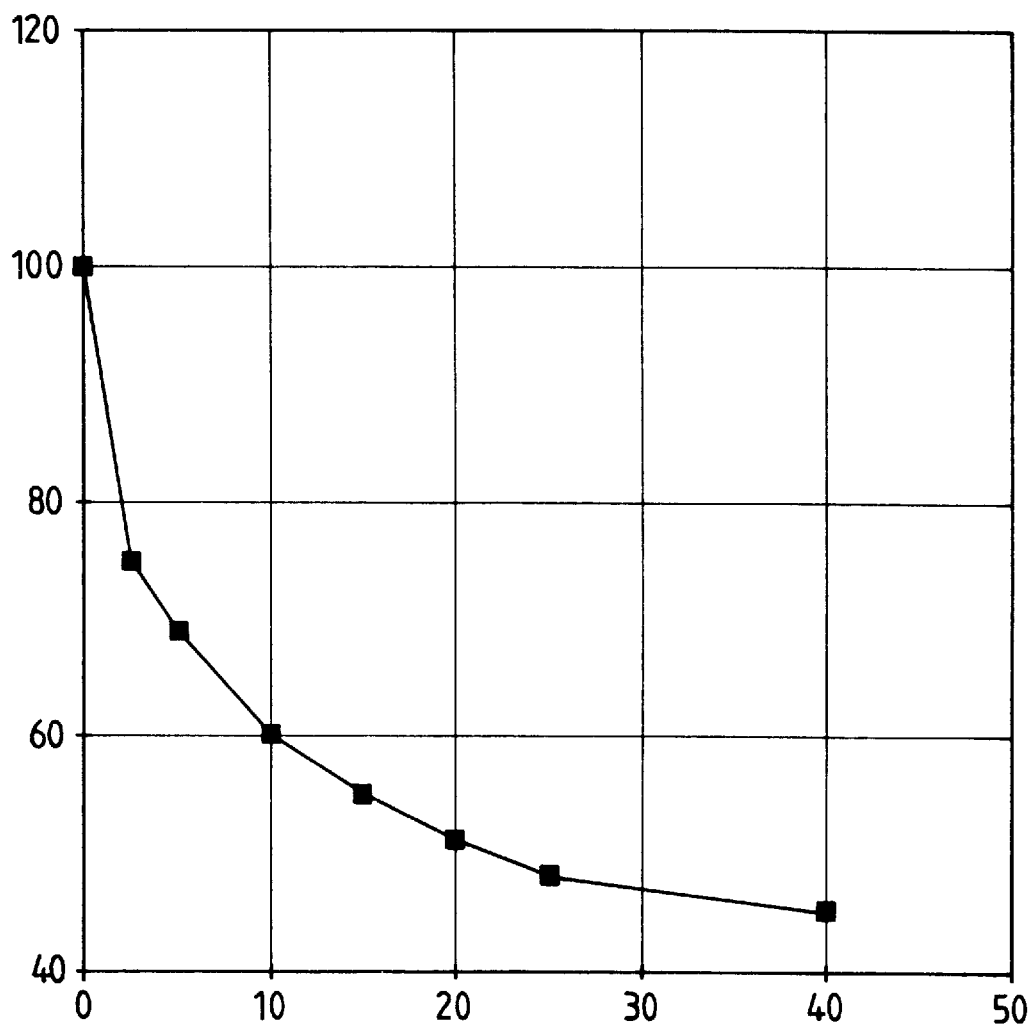
FIG. 3 illustrates the variation of the solidification point of a crude solution of TDA and water.

The variation of the solidification point of a mixture of TDA and water as shown in FIG. 3, is used as the basis for determining suitable concentrations of water in these intermediate mixtures to render the mixtures suitable for storage and/or transportation. FIG. 3 illustrates the solidification points of TDA and water mixtures. More specifically, the TDA comprises 80% by wt. of 2,4-TDA and 20% by wt. of 2,6-TDA The x-axis represents the water content in wt. %, and the y-axis represents the solidification point in °C. According to FIG. 3, a solidification point of, for instance, 65° C. corresponds to a water content of 7 wt. %.

The process used for partial removal of water from a crude solution of TDA and reaction water is much simpler than the apparatus for drying TDA in a conventional process as described above. It is preferred that partial removal of water is via a simple atmospheric pressure distillation. In the process according to the invention, a distillation column having only 5 bubble plates (i.e. practical plates) is more than adequate to produce head products which contain no TDA. Since the major proportion of the water has already been removed in this way, the vacuum distillation apparatus required at the final destination, i.e. a second production plant, to yield dry TDA, needs to only have about 10 plates (i.e. practical plates). Thus, the vacuum distillation apparatus required by the present invention is smaller than the conventional vacuum distillation apparatus required in conventional industrial processes to produce TDA. Accordingly, the distillation apparatus of the present invention is also more economically efficient.

Figure 4:
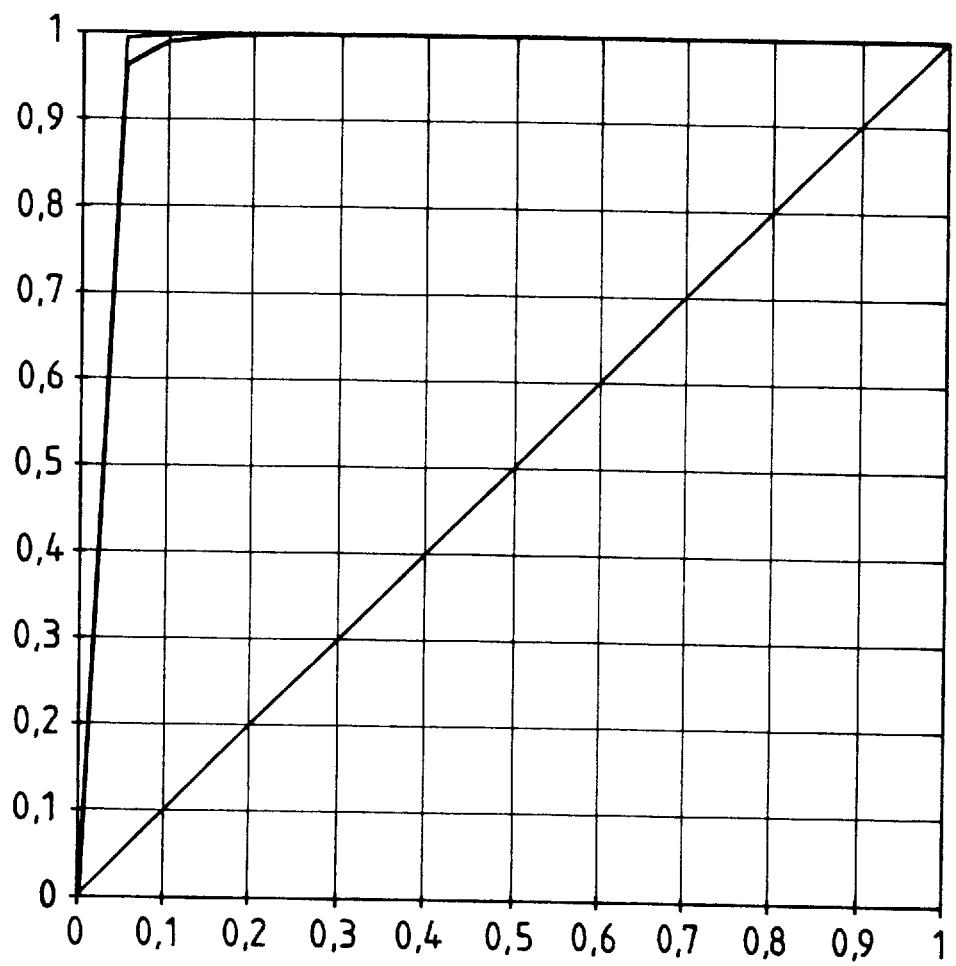
FIG. 4 is a phase equilibrium diagram of the crude solution of TDA and water.

Suitable distillation columns for the present invention to yield dry TDA are designed in a manner known per se, by taking into account the phase equilibrium diagram for the TDA/water (bold: 1013 mbar, thin: 100 mbar) system (see FIG. 4). In FIG. 4, the x-axis represents the molar concentration of water in the liquid phase and the y-axis represents the molar concentration of water in the vapor phase.

A further advantage of the process according to the present invention is the problem-free waste disposal of slops from the ships tanks. Since the ship can be rinsed out with water and the distillation of the intermediate mixture of TDA and water is completed at each ultimate destination, the processing of TDA-containing rinse water is also possible at the final destination. According, expensive special waste incineration procedures are not required.

Further processing of the dried TDA to give TDI at the ultimate (or final) destination is also performed using conventional methods known to those skilled in the art. The 2,3- and 3,4 isomers of TDA and other by-products may, optionally, first be removed from the TDA isomer mixture. Suitable methods for the removal of these isomers and the other by-products are described in, for example, U.S. Pat. Nos. 3,420,752 and 3,414,619, the disclosures of which are herein incorporated by reference. The final step of the overall process to produce TDI by phosgenation of TDA proceeds in a known manner. See, for example, Becker/Braun, Kunststoff-Handbuch, 2nd edition, 1983, vol. 7, p. 63 et seq., Carl-Hanser Verlag, Munich, and the literature cited there.

Accordingly, the present invention provides a process for the production of TDI by nitration of toluene to give dinitrotoluene (DNT), hydrogenation of the DNT to give a crude solution of toluylene diamine (TDA) and reaction water, optionally in the presence of a solvent or diluent, preferably however without the use of these, optionally, completely or partly removing the solvent, and distilling the crude solution of TDA and reaction water to form an intermediate mixture of TDA and water wherein the distillation is stopped at a point such that the intermediate mixture of TDA and water contains from about 1 to 40% by weight of water. This intermediate mixture is then transported from a first production facility to a second production facility. At the second production facility, the intermediate mixture of TDA and water is further distilled to yield dry TDA. Any by-products including, for example, 2,3-TDA and/or 3,4-TDA may also be removed by either this second distillation step or another processing step to yield dry TDA of commercial quality. The dry TDA is then phosgenated to yield TDI.

Suitable compounds for the process according to the invention are 2,4 toluylene diamine and various isomeric mixtures of toluylene diamine. Commercial quality TDA is typically a mixture of the 2,4-isomer and the 2,6-isomer, wherein the isomer ratios of 2,4-TDA to 2,6-TDA are about 65:35 or 80:20. Suitable intermediate mixtures of TDA and water which may be transported from one production plant to a second production plant include isomeric mixtures of 2,4-TDA and/or 2,6-TDA with various concentrations of the 2,3- and 3,4-isomers of TDA. These intermediate mixtures also contain also by-products of the reaction. Typically, the 2,3- and/or the 3,4-isomers are present in these intermediate mixtures in quantities of from about 0.05 to 5.0 wt. %. These intermediate mixtures of TDA and water also contain various proportions of by-products having high molecular weights. These higher molecular weight by-products typically are present in quantities of from about 0.01 to 2.5 wt. %, usually 0.2 to 1.8 wt. %.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

Production of a TDA/water mixture according to the invention a) Preparation of dinitrotoluene:

Dinitrotoluene (DNT) was prepared in two stirred tank reactors which were cooled with water. Each reactor had a working volume of 500 l and was equipped with a lateral overflow into separating flasks, each flask having a volume of 100 l. On the degassing side, the apparatus was connected to a vent gas collection line which was operated at atmospheric pressure. Before starting-up the reaction, both vessels were filled with 92% strength sulfuric acid to the overflow the stirrer was switched on.

Into the first tank were fed 93 kg/h of toluene and 100 kg/h of 65% strength nitric acid as well as sulfuric acid which had been introduced into the second tank as 92% strength acid at 665 kg/h and had overflowed into the downstream settling flask.

The overflow from the first tank separated, in the associated settling flask, into a sulfuric acid phase, which was removed for processing, and an organic phase which consisted mainly of mononitrotoluene (MNT). The organic phase was continuously pumped into the second tank, where, in addition to the 92% sulfuric acid mentioned above, another 105 kg/h of 65% strength nitric acid was added. The temperature in the second tank was 70° C.

The overflow from the second tank separated, in the associated settling flask, into a sulfuric acid phase as mentioned above, which was then pumped into the first tank, and an organic phase which contained crude DNT and entrained traces of acid.

To purify the product, the crude DNT was passed continuously through a 3-stage mixer/settler battery maintained at 70° C. wherein the crude DNT was washed, in sequence, with 50 l/h of warm water (70° C.), 50 l/h of 2% strength caustic soda solution (70° C.), and 50 l/h of deionized water (70° C.). An aqueous extract of the resulting DNT had a pH of 7.6. The aqueous phase was rejected as effluent.

b) Hydrogenation of DNT to yield TDA:

A 500 l autoclave equipped with cooling and heating facilities, a gas dispersion stirrer, a thermometer and a level indicator was used to hydrogenate DNT to yield toluylene diamine (TDA).

A mixture of 70 kg of water and 150 kg of toluylene diamine at 80° C. were initially introduced into the autoclave, and then about 7 kg of Raney nickel, suspended in about 30 l of water were added to this mixture. The autoclave was filled 10 times with hydrogen at a pressure of 10 bar, and then decompressed to atmospheric pressure each time. Hydrogen was then introduced at a pressure of 22 bar, the stirrer was switched on, and the addition of DNT into the reaction mixture, via a submerged tube, at a rate of 182 kg/h was started.

After about 2 minutes, initiation of reaction was detected by means of the rapid increase in temperature inside the autoclave. After changing the heating procedure to a cooling procedure, the temperature was controlled at 190° C. Hydrogen consumption was compensated for by adding fresh hydrogen such that the pressure inside the autoclave was maintained constant at 22 bar. A gas stream of 25 $Nm^3$/h was withdrawn from the gas space in the autoclave.

When the liquid had filled 75% of the autoclave, the withdrawal of product via an immersion tube was started. The product flowed into a filtration vessel having a capacity of about 20 l, in which a 3$\mu$ sintered metal filter cartridge was previously inserted.

About 50 l/h of reaction mixture enriched with catalyst was returned from the filtration vessel to the reactor using a pump, while the pressure of the reaction mixture flowing through the filter cartridge was reduced to 3 bar in a decompression container with a reflux condenser, via a regulating valve which was controlled by the level in the reactor. The decompressed gases were discharged as vent gas.

The reaction mixture flowed continuously from the decompression container into the first distillation column with 5 bubble plates, wherein the distillation column was about 2.5 m in length and about 200 mm in diameter. The column was operated at ambient pressure and the base was heated to 135° C. using a plug-in evaporator and 6 bar steam. At the head of the column, water containing about 25 ppm of TDA was withdrawn at a reflux ratio (reflux/take off)=3. The product from the base of the column was an intermediate mixture of TDA and water which contained about 7% by wt. water, and had a solidification point of about 65° C. This product contained a mixture of the various isomers of TDA, namely the 2,3-, 2,4, 3-4- and 2,6-isomers, as well as of by-products of TDA having higher molecular weights. No solids settled out of this intermediate mixture of TDA and water after being stored for 4 weeks at about 70° C. Thus, this intermediate mixture of TDA and water was suitable for bulk transport at 70° C. in a ship.

Example 2

Production of toluylene diisocyanate from an intermediate mixture of TDA and water according to the invention Residual water was removed from the intermediate mixture of TDA and water (i.e. the product from the first distillation column described in Example 1b above) under vacuum at 100 mbar at the top and 205° C. in the sump. in a second distillation column with 10 bubble plates. This second distillation column was about 4.5 m in length and about 300 mm in diameter. The base of the column was heated using 30 bar steam. This distillation yielded essentially dry TDA (which contained about 400 ppm of water) at the base of the column, with water being produced at the head of column (which contained about 10 ppm of TDA) when (reflux/take off)=4.

Figure 2:
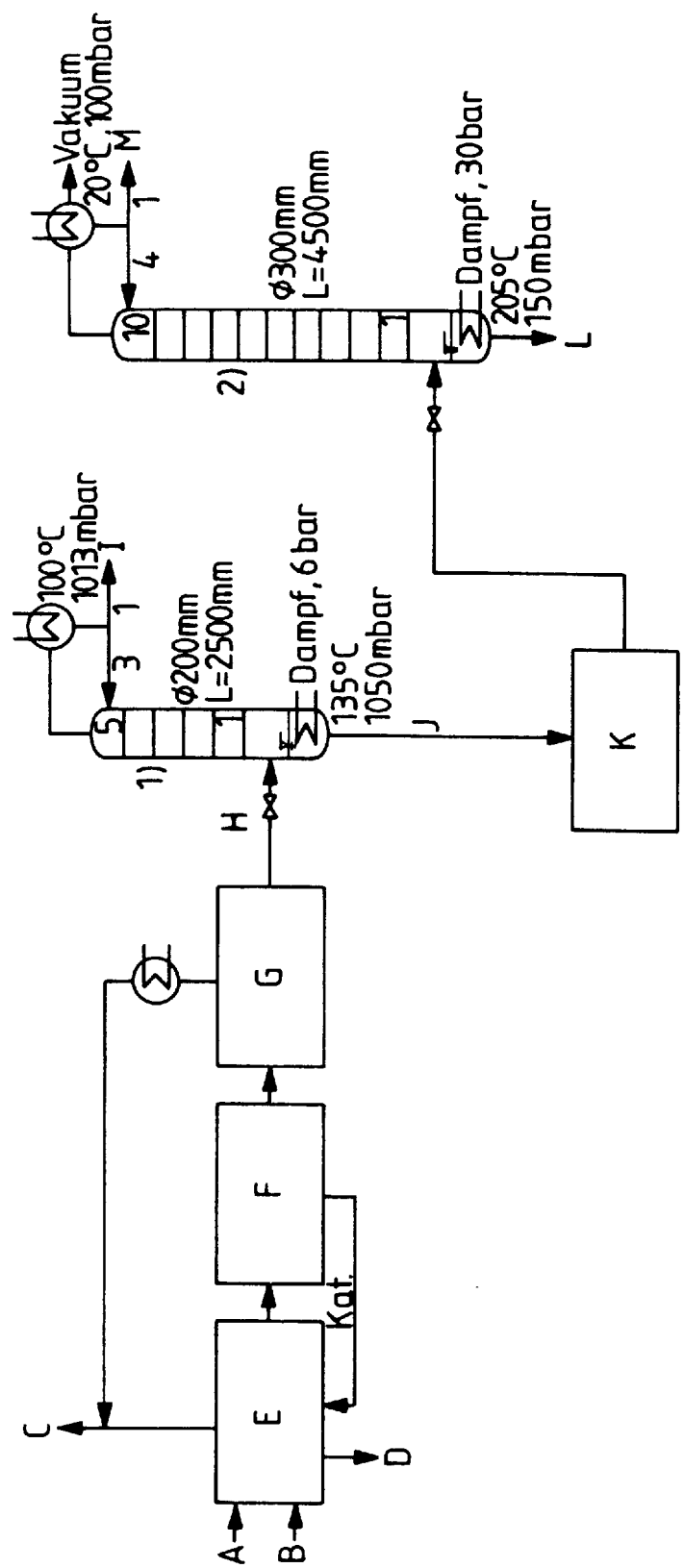
FIG. 2 is a schematic diagram illustrating the process according to the present invention, through the second distillation step.

A schematic diagram of the process according to the present invention, through the second distillation step, is shown in FIG. 2. In FIG. 2:

A represents: DNT supply;

B represents: Hydrogen supply;

C represents: Vent gas;

D represents: Heat removal;

E represents: Catalytic conversion of DNT to TDA (185° C., 25–30 bar, 2–3 wt. % of catalyst);

F represents: Catalyst separation;

G represents: Decompressing to 130° C., 3 bar;

H represents: Supply to column 1;

I represents: Water withdrawal (TDA content: 25 ppm);

J represents: Withdrawal of intermediate; mixture of TDA and water (in accordance with the invention);

K represents: Temporary storage and/or transportation of intermediate mixture of TDA and water (in accordance with the present invention), at 80° C.;

L represents: Withdrawal of TDA from column 2 (water content: 400 ppm)

M represents: Water withdrawal from column 2 (TDA content: 10 ppm)

1) represents: First distillation column wherein:
  5 represents: the number of bubble plates in column 1; and 2) represents: Second distillation column wherein:
  10 represents: the number of bubble plates in column 2.

The dry TDA was then reacted with phosgene to yield TDI. This stage was performed in a continuously operated apparatus which essentially consisted of two stirred tanks heated with 30 bar steam, each having a capacity of 2 m$^3$, and two distillation columns.

800 kg/h of phosgene in the form of a 50% strength solution in ortho-dichlorobenzene (ODB) was fed into the first of the two stirred tanks, and heated to 90° C. at a pressure of 1.9 bar. The overflow flowed into the second stirred tank which was connected to the-first tank on the degassing side and was maintained at a temperature of about 135° C.

TDA, which was withdrawn from a TDA solution tank at 120 kg/h at 45° C. in the form of a 5% strength solution in ODB via a pump, was mixed with the phosgene solution which was introduced into the first stirred tank. A centrifugal pump with an open impeller was used to intensively mix the two solutions.

After leaving the second stirred tank, the reaction mixture was heated to 190° C. in a heat exchanger operated with 30 bar steam.

The vapors discharged from the stirred tanks and from the heat exchanger were passed through a wash column having a diameter of about 500 mm, a length of about 4 m and containing 10 bubble plates. A condenser cooled with ODB at 60° C. at the head of the column condensed out some of the reaction mixture which was added to the column as reflux medium. The discharge from the column was returned to the first stirred tank below the liquid level. The vapors emerging from the column were passed into a recovery apparatus to separate the excess phosgene used from the hydrogen chloride produced.

The reaction mixture at 190° C. emerging from the heat exchanger (mentioned above) was introduced into the base of the solvent column which had a diameter of about 450 mm, a length of about 6 m and contained packing to a height of about 4 m. The base of the solvent column was heated to about 185° C. with 30 bar steam using a plug-in evaporator, and the pressure at the head of the column was 330 mbar. A reflux ratio R:E=2 was established using a condenser operating with cold water. The ODB withdrawn contained no TDI and was used again to prepare the TDA solution and phosgene solution (as described above which entered the first tank).

The TDI withdrawn from the base of the solvent column was heated with about 10% ODB in a downstream thin-layer evaporator (TLE), which was heated with 30 bar steam and maintained at a pressure of 100 mbar, and the ODB was completely removed. The TLE distillate was condensed in a condenser using cold water and returned to the solvent column.

The discharge from the base of the TLE was separated into approximately 90% head product and about 10% bottoms product in a second thin layer evaporator which was also heated with 30 bar steam and maintained at a pressure of 10 mbar. The bottoms product was collected in a distillation boiler with a volume of 2 m$^3$ and evaporated down batchwise using 30 bar steam at 220° C./5 mbar until a viscous melt had formed. This viscous melt was run off while hot, solidified in cardboard tubs, and disposed of by a waste incineration procedure. This melt contained high boiling by-products which were formed during phosgenation, as well as the higher molecular weight by-products from the TDA-feed.

The distillate from boiler distillation was fed, together with the distillate from the second TLE, to the TDI column.

The TDI column had a total height of about 5 m, a diameter of 250 mm and contained packing to a height of about 3.5 m. At the head of the column was a condenser which produced total reflux. Product withdrawal from the TDI column took place about 400 mm below the top of the internal packing by means of a withdrawal plate. The reflux ratio R:E was 15. There was a pressure of 15 mbar at the head of the column.

The base of the TDI column had a volume of about 100 l and was heated with 30 bar steam by means of a plug-in evaporator so that the temperature was 163° C. The contents of the base portion were reduced by about 30 l at regular intervals of 6 h and the product withdrawn was added to the feedstock to the second TLE mentioned above.

The TDI product withdrawn from the TDI column had the following analytical characteristics:

| | |
|---|---|
| 79.4% | 2,4-isomer |
| 20.6% | 2,6 isomer |
| 0.005% | hydrolyzable chlorine |
| and | |
| less than 0.005% | ODB. |

Therefore, the TDI product of this example corresponded to the quality of commercial TDI.

The yield over all the manufacturing stages from toluene to toluylene diisocyanate was about 85%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of toluylene diisocyanate comprising the steps of:

1) reacting toluene with nitric acid to yield dinitrotoluene,
   2) hydrogenating said dinitrotoluene to form a crude solution of toluylene diamine and reaction water,
   3) distilling said crude solution of toluylene diamine and reaction water to form an intermediate mixture of toluylene diamine and water, said distillation being interrupted at a point wherein the water content of said intermediate mixture is from about 1 to 40% by weight,
   4) transporting said intermediate mixture of toluylene diamine and water from a first production plant to a second production plant,
   followed by
   5) distilling said intermediate mixture of toluylene diamine and water completely at the second production plant to yield dry toluylene diamine,
   and
   6) phosgenating said dry toluylene diamine to yield toluylene diisocyanate.

2. The process of claim 1, wherein hydrogenating said dinitrotoluene is in the presence of a solvent or diluent, and is followed by removing said solvent or diluent, either partially or completely, from said crude solution of toluylene diamine prior to distilling said crude solution of toluylene diamine and reaction water to yield said intermediate mixture of toluylene diamine and water.

3. The process of claim 1, wherein distilling said crude solution of toluylene diamine and reaction water to yield said intermediate mixture of toluylene diamine and water is interrupted at a point wherein the water content of said intermediate mixture is from about 2 to 10% by weight.

4. The process of claim 1, wherein said toluylene diamine comprises the 2,4-isomer, the 2,6-isomer, or mixtures thereof.

5. The process of claim 4, wherein said toluylene diamine comprises the 2,4-isomer, the 2,6-isomer, or mixtures thereof, in combination with the 2,3-isomer, the 3,4-isomer, or mixtures thereof.

6. In a process for the production of toluylene diisocyanate comprising phosgenating toluylene diamine to yield toluylene diisocyanate, the improvement wherein said toluylene diamine comprises a mixture of toluylene diamine and reaction water which contains 1 to 40% by weight of reaction water, said mixture having a freezing point of at most 95° C., and being an intermediate mixture formed by partially distilling a crude solution of toluylene diamine and reaction water, which was completely distilled to remove the reaction water content prior to being subjected to phosgenation.

7. A process for the production of toluylene diisocyanate comprising the steps of:

1) reacting toluene with nitric acid to yield dinitrotoluene,
   2) hydrogenating said dinitrotoluene to form a crude solution of toluylene diamine and reaction water,
   3) distilling said crude solution of toluylene diamine and reaction water to form an intermediate mixture of toluylene diamine and water, wherein said intermediate mixture of toluylene diamine and water having a freezing point of at most 95° C.,
   4) transporting said intermediate mixture of toluylene diamine and water from a first production plant to a second production plant which is spatially displaced from the first production plant,
   followed by
   5) distilling said intermediate mixture of toluylene diamine and water completely at the second production plant to yield dry toluylene diamine,
   and
   6) phosgenating said dry toluylene diamine to yield toluylene diisocyanate.

* * * * *